United States Patent
Emken et al.

(10) Patent No.: US 11,550,167 B2
(45) Date of Patent: Jan. 10, 2023

(54) OPHTHALMIC DEVICE WITH BLEND ZONES AND ALIGNMENT SIDEWALLS

(71) Applicant: Verily Life Sciences LLC, South San Francisco, CA (US)

(72) Inventors: Jeremy Emken, Belmont, CA (US); Scott Kennedy, Anderson, IN (US); Kristopher Lavery, Pleasanton, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 460 days.

(21) Appl. No.: 16/709,184

(22) Filed: Dec. 10, 2019

(65) Prior Publication Data

US 2020/0183187 A1 Jun. 11, 2020

Related U.S. Application Data

(60) Provisional application No. 62/777,896, filed on Dec. 11, 2018.

(51) Int. Cl.
*G02C 7/08* (2006.01)
*A61F 2/16* (2006.01)
(Continued)

(52) U.S. Cl.
CPC ............ *G02C 7/083* (2013.01); *A61F 2/1627* (2013.01); *G02C 7/04* (2013.01); *A61F 2/482* (2021.08); *A61F 2250/0003* (2013.01)

(58) Field of Classification Search
CPC .................... A61F 2/482; A61F 2/1627; A61F 2250/0003; G02C 7/083; G02C 7/04
See application file for complete search history.

(56) References Cited

U.S. PATENT DOCUMENTS

| 5,219,497 | A | 6/1993 | Blum |
| 6,319,433 | B1 | 11/2001 | Kohan |

(Continued)

FOREIGN PATENT DOCUMENTS

| CN | 106104358 A | 11/2016 |
| CN | 108474959 A | 8/2018 |

OTHER PUBLICATIONS

International Search Report and Written Opinion, dated Feb. 28, 2020, in corresponding International Patent Application No. PCT/US2019/65748, 8 pages.
(Continued)

*Primary Examiner* — William H Matthews
(74) *Attorney, Agent, or Firm* — Christensen O'Connor Johnson Kindness PLLC

(57) ABSTRACT

Ophthalmic devices and ophthalmic systems including alignment sidewalls and blend zones disposed therethrough are described. An example ophthalmic device may include a first and a second optical element having alignment sidewalls shaped to cooperatively couple. The alignment sidewall may include blend zones disposed in the sidewall shaped to transition the sidewall from a ridge to a surface of an optic zone of the optical element. The alignment sidewalls may define a cavity disposed between two coupled optical elements when the alignment sidewalls are cooperatively coupled into which a liquid crystal may be disposed. A method of assembling an ophthalmic device is described. An example method may include aligning a blend zone of a first optical element with a mating blend zone of a second optical element. The example method may further include cooperatively coupling alignment sidewalls of the first optical element and the second optical element.

20 Claims, 10 Drawing Sheets

(51) Int. Cl.
    *G02C 7/04*         (2006.01)
    *A61F 2/48*         (2006.01)

(56) References Cited

U.S. PATENT DOCUMENTS

| | | |
|---|---|---|
| 6,491,394 B1 | 12/2002 | Blum et al. |
| 7,019,890 B2 | 3/2006 | Meredith |
| 7,499,223 B2 | 3/2009 | Berge et al. |
| 9,182,521 B2 | 11/2015 | Pugh et al. |
| 9,335,562 B2 | 5/2016 | Pugh et al. |
| 9,841,614 B2 | 12/2017 | Linhardt et al. |
| 10,139,529 B2 | 11/2018 | Meneghini et al. |
| 2004/0169932 A1 | 9/2004 | Esch et al. |
| 2005/0185135 A1 | 8/2005 | Blum et al. |
| 2008/0123049 A1* | 5/2008 | Volk ................ B29D 11/00028 351/159.41 |
| 2010/0109175 A1* | 5/2010 | Pugh ........................ G02C 7/04 264/1.36 |
| 2012/0019773 A1 | 1/2012 | Blum et al. |
| 2014/0192313 A1 | 7/2014 | Riall et al. |
| 2015/0029424 A1 | 1/2015 | Gordon et al. |
| 2016/0170097 A1* | 6/2016 | Milton .................. G02C 7/041 349/200 |
| 2016/0276678 A1 | 9/2016 | Jorgensen et al. |
| 2018/0088351 A1 | 3/2018 | Kennedy et al. |
| 2018/0088354 A1 | 3/2018 | Emken et al. |

OTHER PUBLICATIONS

First Chinese Office Action dated Mar. 18, 2022, in corresponding Chinese Application No. 201980081264.5 (Chinese version), filed Dec. 11, 2019, 6 pages.

\* cited by examiner

OPHTHALMIC DEVICE WITH BLEND ZONES AND ALIGNMENT SIDEWALLS

CROSS-REFERENCE TO RELATED APPLICATION

This application claims the benefit of U.S. Provisional Application No. 62/777,896, filed Dec. 11, 2018, which is hereby incorporated by reference in its entirety.

TECHNICAL FIELD

This disclosure relates generally to ophthalmic devices and, in particular but not exclusively, relates to accommodating ophthalmic devices.

BACKGROUND INFORMATION

Presbyopia may be treated with wearable or implantable lenses that provide accommodation. For example, a lens may provide accommodation through electrical stimulation of liquid crystal material included in the lens. The lenses, either implanted or worn on the surface of the eye similar to a contact lens, may include multiple layers of material to provide the accommodation and associated control.

The multiple layers, however, may complicate fabrication of the lens due to the size of the components that form the multiple layers and alignment requirements. For example, an optical axis of the lens may add an alignment constraint to the fabrication of the lens. Misalignment of optical axes of the multiple layers may result in blurred vision. While many fabrication techniques may be available to provide the desired alignment, additional factors of the lens may not be addressed by such techniques.

BRIEF DESCRIPTION OF THE DRAWINGS

Non-limiting and non-exhaustive embodiments of the claimed subject matter are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of a system and an apparatus including ophthalmic devices including alignment sidewalls and blend zones are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1:
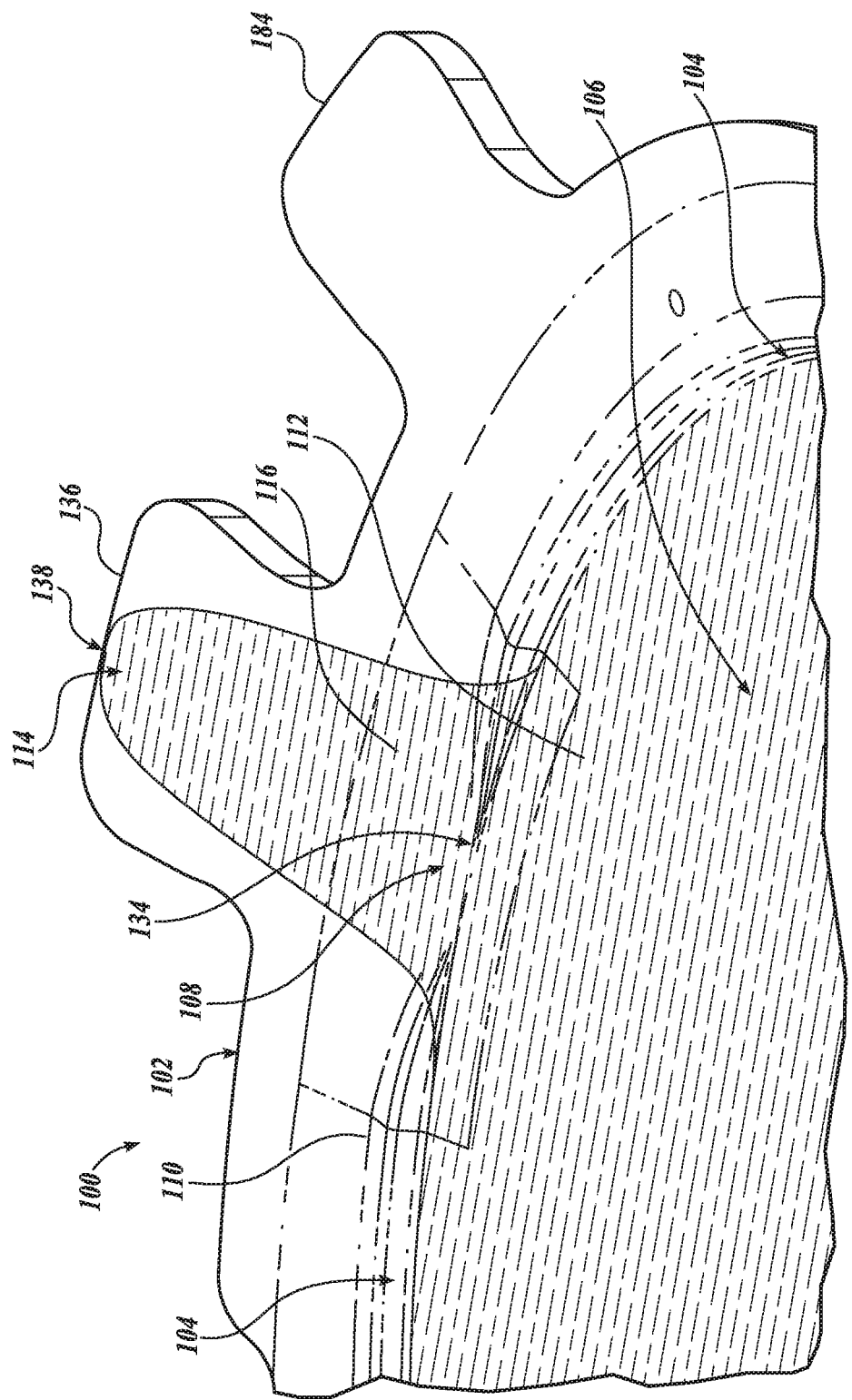
FIG. 1 is a partial isometric view of an optical element, in accordance with an embodiment of the disclosure.

FIG. 1 is a partial isometric view of an optical element 102, in accordance with an embodiment of the disclosure. As discussed further herein, optical element 102 can be a component of an ophthalmic device 100 including additional optical elements (not shown, see for example FIGS. 2A-2C) shaped to couple with or otherwise assemble in a stacked configuration. As shown, optical element 102 includes an alignment sidewall 104, a blend zone 108, and a conductive layer 116. In the illustrated embodiment, the alignment sidewall 104 is disposed about an optic zone 106 of the optical element 102. In this regard, the alignment sidewall 104 is not visible by a user when, for example, the optical element 102 is mounted on or in an eye. Alignment sidewall 104 includes an alignment sidewall ridge 110 protruding from a surface 112 of the optic zone 106. As discussed further herein with respect to FIGS. 2A-2C, the alignment sidewall 104 is shaped to cooperatively couple with an alignment sidewall of another optical element. Such cooperative coupling is suitable to, for example, align an optical axis of the optical element 102 and an optical axis of the other optical element (not shown, see FIGS. 2A-2C) and to provide a cavity disposed adjacent to the optic zone 106 and between optical elements.

As shown, blend zone 108 is disposed in the alignment sidewall 104 and shaped to transition the alignment sidewall 104 from ridge 110 of the alignment sidewall 104 to a surface 112 of the optic zone 106. In this regard, blend zone 108 forms a pathway 114 through the alignment sidewall 104. Optical element 102 further includes conductive layer 116 being optically transmissive. As shown, conductive layer 116 is disposed on the surface 112 of the optic zone 106 and extending through the pathway 114 of the blend zone 108.

As above, the conductive layer 116 is also optically transmissive. In an embodiment, the conductive layer 116 is electrically conductive. In this regard, and as discussed further herein with respect to FIGS. 2A-2C, the conductive layer 116 is suitable to apply an electrical potential to a liquid crystal (not shown, see FIG. 4) disposed between optical elements, while being optically transmissive such that a user can see through the conductive layer 116. In an embodiment, the conductive layer 116 includes a plurality of electrically conductive metal nanowires, such as silver nanowires. While conductive layers including electrically conductive metal nanowires are discussed herein, it will be understood that the conductive layers of the present disclosure encompass other optically transmissive, electrically conductive materials, such as indium tin oxide, aluminum-doped zinc-oxide, barium stannate, doped polythiophenes, such as poly(3,4-ethylenedioxythiophene) polystyrene sulfonate, and the like.

In the illustrated embodiment, conductive layer 116 is disposed within the pathway 114 of blend zone 108. Optical element 102 is shown to include a conductive tab 136 in electrically conductive communication with the conductive layer 116 disposed in pathway 114. In an embodiment, a central portion 134 of the blend zone 108, such as pathway 114, is curvature continuous with a curvature of optic zone 106. See for example FIGS. 3B and 3C. As shown, conductive tab 136 is disposed at a periphery 138 of optical element 102. Further, in an embodiment, a center of pathway 114 is aligned with a center of conductive tab 136. Such peripheral placement of conductive tab 136 is suitable to electrically couple the conductive tab 136 with such an external power source. In this regard, electrical signals, electrical power, and the like can be provided to conductive layer 116 through conductive tab 136 from an exterior source (not shown, see for example FIGS. 2A-2C), such as a controller.

Figure 2A:
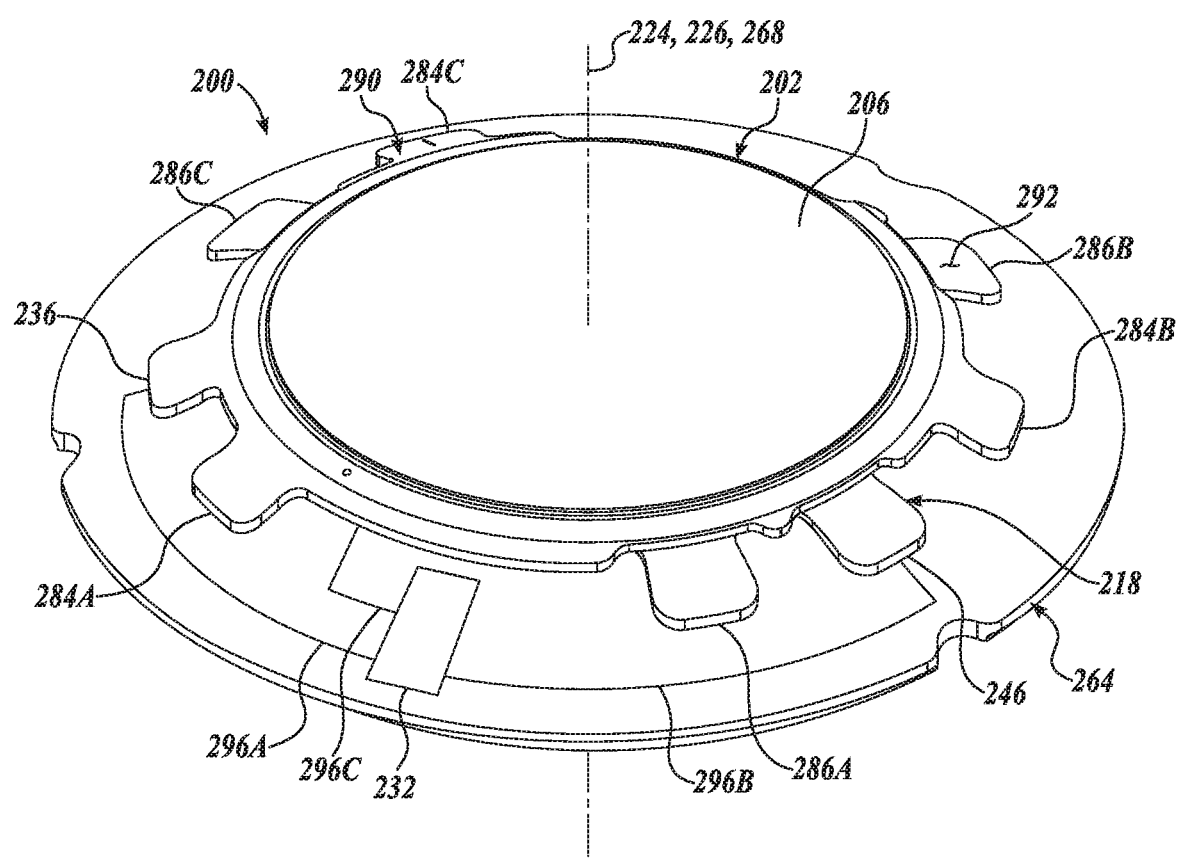
FIG. 2A is an isometric view of an ophthalmic device, in accordance with an embodiment of the disclosure.
Figure 2B:
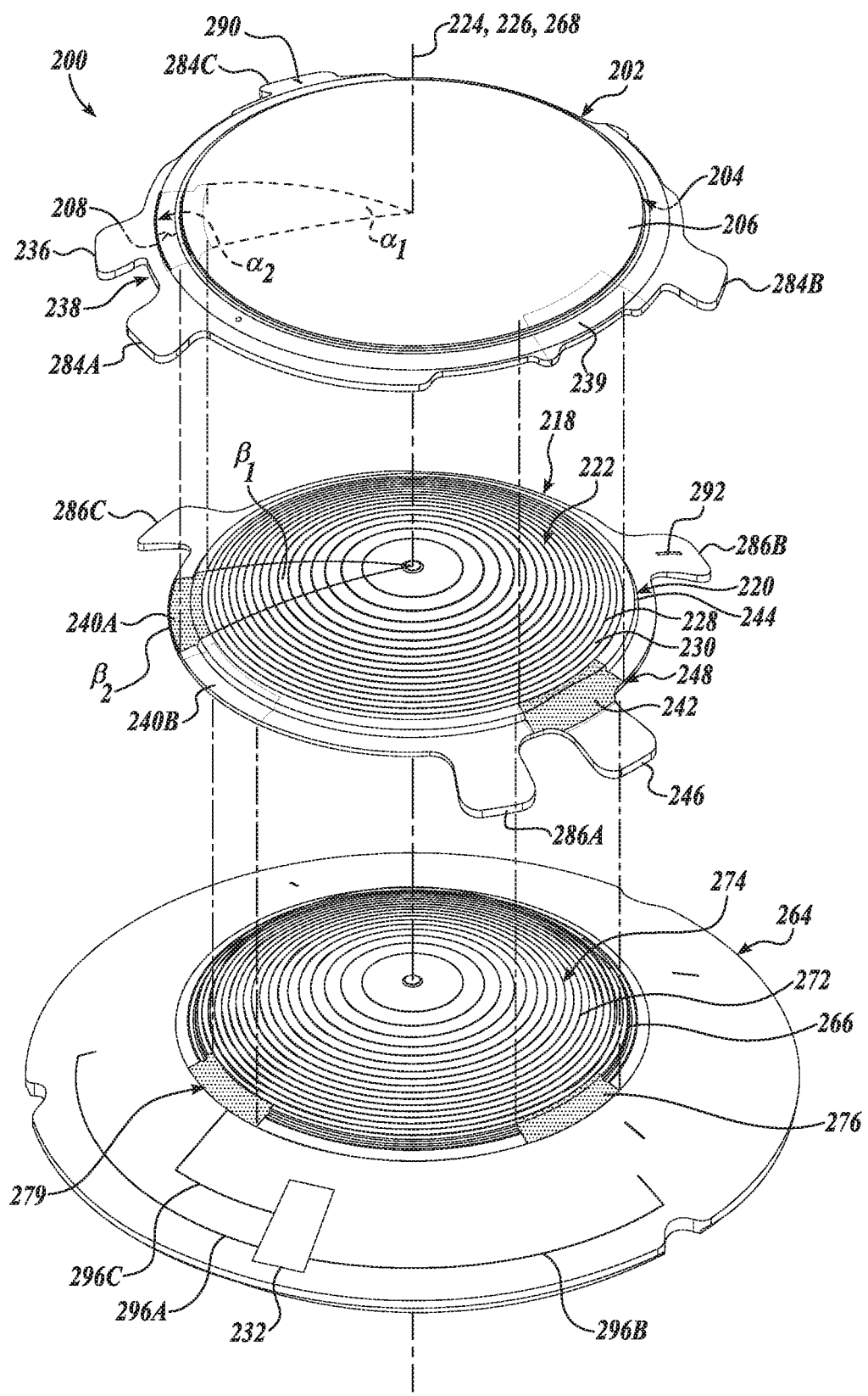
FIG. 2B is a top-down isometric exploded view of the ophthalmic device of FIG. 2A, in accordance with an embodiment of the disclosure.
Figure 2C:
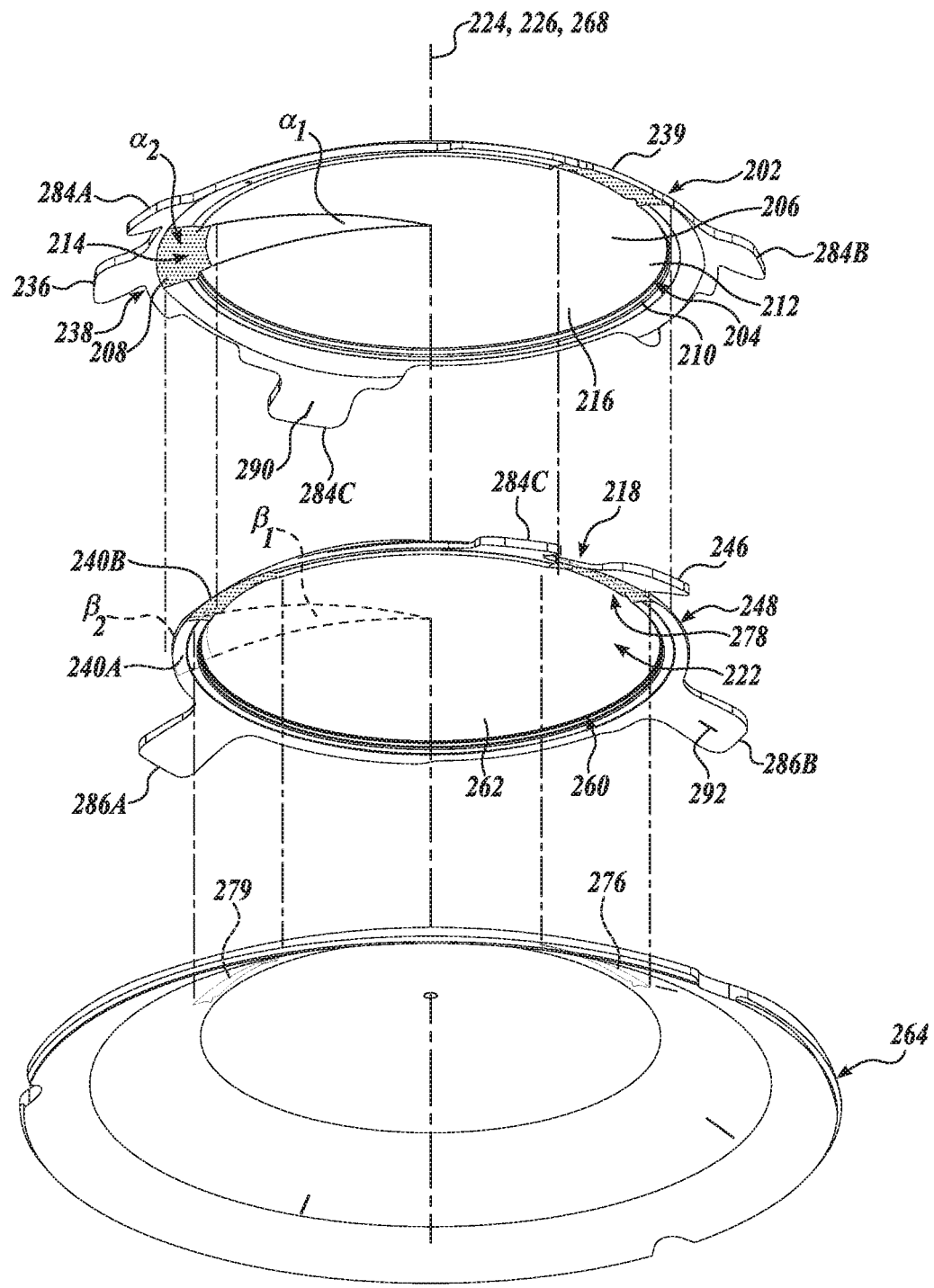
FIG. 2C is a bottom-up isometric exploded view of the ophthalmic device of FIG. 2A, in accordance with an embodiment of the disclosure.

FIG. 2A is an isometric view of an ophthalmic device 200, in accordance with an embodiment of the disclosure. FIG. 2B is a top-down isometric exploded view of the ophthalmic device 200, in accordance with an embodiment of the disclosure. FIG. 2C is a bottom-up isometric exploded view of the ophthalmic device 200, in accordance with an embodiment of the disclosure.

Ophthalmic device 200 is shaped to be mounted on and/or implanted in an eye. Accordingly, in an embodiment, ophthalmic device 200 is an accommodating ophthalmic device, such as an accommodating intraocular lens or an accommodating contact lens. In an embodiment, ophthalmic device 200 is shaped to be mounted on a surface of an eye, such as a corneal surface. In another embodiment, ophthalmic device 200 is shaped to be implanted in an eye, such as in a capsular bag of an eye.

Ophthalmic device 200 is shown to include a first optical element 202 and a second optical element 218. In an embodiment, first optical element 202 is an example of optical element 102. As shown, first optical element 202 and second optical element 218 are shaped to cooperatively couple to align a first optical axis 224 of first optical element 202 and a second optical axis 226 of second optical element 218. In this regard, optical axes 224 and 226 are center optical axes of optical elements 202 and 218, respectively, and optical elements 202 and 218 are coaxially aligned when optical elements 202 and 218 are coupled. As discussed further herein, misalignment of optical axes of the multiple layers may result in blurred vision when ophthalmic device 200 is mounted on or in an eye.

In the illustrated embodiments, first optical element 202 includes a first alignment sidewall 204 disposed about first optic zone 206 and second optical element 218 includes second alignment sidewall 220 disposed about a second optic zone 222. As shown, the first alignment sidewall 204 and second alignment sidewall 220 shaped to cooperatively couple. In this regard, as first optical element 202 and second optical element 218 cooperatively couple, first optical axis 224 and second optical axis 226 are aligned.

In an embodiment, first alignment sidewall 204 has an angle relative to first optical axis 224 in a range of about 2° to about 15°. In an embodiment, first alignment sidewall 204 has an angle relative to first optical axis 224 in a range of about 5° to about 15°. Such relatively steep alignment sidewall angles are suitable to closely align first optical axis 224 and second optical axis 226 when first alignment sidewall 204 and second alignment sidewall 220 are cooperatively coupled. In this regard, in an embodiment, first optical axis 224 and second optical axis 226 are disposed in a range of about 0 µm to about 30 µm when first alignment sidewall 204 and second alignment sidewall 220 are cooperatively coupled.

Conductive layers, such as those including silver nanowires, tend not to coat evenly such steep sidewalls and/or provide even, reliable electrical communication to electrical power sources disposed outboard of the steep sidewalls. Accordingly, while relatively steep alignment sidewalls are suitable to provide closely aligned optical axes of optical elements, such steep sidewalls generally make difficult electrical connection between conductive layers disposed in optical zones of optical elements and electrical connectors disposed outboard of alignment sidewalls.

In this regard, first optical element 202 includes a blend zone 208 disposed in the first alignment sidewall 204. As illustrated, first blend zone 208 is disposed rotationally asymmetrically with respect to first optical axis 224. As discussed further herein with respect to FIG. 1, blend zone 208 is shaped to transition the first alignment sidewall 204 from a ridge 210 of the first alignment sidewall 204 to a surface 212 of the first optic zone 206 to form a pathway 214 through the first alignment sidewall 204. First conductive layer 216 being optically transmissive is disposed on surface 212 of the first optic zone 206 and extends through the pathway 214 of the blend zone 208. In this regard, first conductive layer 216 is in electrically conductive communication with conductive tab 236 disposed about periphery 238 of first optical element 202 and with controller 232 through conductive trace 296A.

This is in contrast to other portions of conductive layer 216 an outer extent of which are defined at least in part by first alignment sidewall 204. As above, in certain embodiments, the conductive layer 216 includes a plurality of electrically conductive silver nanowires. Such silver nanowires may be applied to surface 212 through, for example, application of a suspension of silver nanowires and a solvent, which is evaporated. The conductive characteristics, such as an electrical resistance, of conductive layer 216 are generally higher when the suspension of conductive nanowires is placed on a smooth, even surface. For example, where such a suspension is applied to a surface having a ridge, a conductive layer made therefrom may have an uneven electrical resistance. In contrast, conductive layer 216 disposed on surface 212 and in pathway 214 has an even resistance suitable for conducting electrical signals, power, and the like from an outside source.

Blend zone 208 is shown to have an angle $\alpha_1$ an arc length $\alpha_2$ relative to the first optical axis 224. In an embodiment, angle $\alpha_1$ is in a range of about 10° to about 50°. In an embodiment, angle $\alpha_1$ is in a range of about 15° to about 40°. As discussed further herein, in an embodiment, conductive layers 216 and 228 include conductive metal nanowires, such as silver nanowires. As angle $\alpha_1$ narrows, the width of the conductive path 214 is reduced, thus generally increasing electrical resistance through the conductive layer 216 in the blend zone 208 region. Such increased electrical resistance may be higher than, for example, an electrical power capability of an implanted accommodating intraocular ophthalmic device 200. Accordingly, in embodiment, angle $\alpha_1$ is greater than about 10°.

Second optical element 218 includes a second conductive layer 228 being optically transmissive and disposed on a surface 230 of the second optic zone 222 facing the first optical element 202. As discussed further herein with respect to FIG. 4, such facing conductive layers 216 and 228 are suitable to apply an electrical potential to liquid crystals (not shown, see FIG. 4) disposed between adjacent optical elements 202 and 218, thereby changing an optical power of the ophthalmic device 200. In that regard, ophthalmic device 200 further includes a controller 232, such as a controller including a power source, operably coupled to conductive layers 216 and 228, suitable to apply a voltage to first conductive layer 216 and second conductive layer 228. In an embodiment, controller 232 includes logic that when executed by the controller 232 causes the ophthalmic device 200 to perform operations. In an embodiment, such operations include applying a voltage to the first conductive layer 216 and the second conductive layer 228, thereby changing an optical power of the ophthalmic device 200, such as by changing a refractive index of a liquid crystal disposed between optical elements 202 and 218.

In the illustrated embodiment, second optical element 218 includes a mating blend zone 240A shaped to cooperatively couple with the blend zone 208 disposed on first optical element 202. In this regard, the first alignment sidewall 204 and the second alignment sidewall 220 cooperatively couple without the second alignment sidewall 220 contacting blend zone 208 with second alignment sidewall ridge 244. Rather, as discussed further herein with respect to FIG. 3B, as blend zone 208 transitions the first alignment sidewall 204 from a ridge 210 of the first alignment sidewall 204 to a surface 212 of the first optic zone 206, mating blend zone 240A likewise transitions the second alignment sidewall 220 from a ridge of the second alignment sidewall 220 to a surface 230 of the second optic zone 222.

In an embodiment, mating blend zone 240A has an angle $\beta_1$ and an arc length $\beta_2$ relative to the second optical axis 226. In an embodiment, angle $\beta_1$ and arc length $\beta_2$ are smaller than angle $\alpha_1$ and an arc length $\alpha_2$, respectively, of the blend zone 208. In this regard, the relative sizes of arc lengths $\beta_2$ and $\alpha_2$ provide rotational tolerance in cooperatively coupling first alignment sidewall 204 and second alignment sidewall 220, such as during manufacturing and assembly of ophthalmic device 200.

As discussed further herein, in an embodiment, ophthalmic device 200 is configured to apply a voltage to conductive layer 216 and to conductive layer 228. In that regard, in an embodiment, the second optical element 218 includes a second blend zone 242 disposed in the second alignment sidewall 220 and shaped to transition the second alignment sidewall 220 from a second alignment sidewall ridge 244 of the second alignment sidewall 220 to a surface 230 of the second optic zone 222. Such a second blend zone 242 forms a pathway through the second alignment sidewall 220. As shown, the second conductive layer 228 is disposed on and extending through the pathway of the second blend zone 242 and disposed on the second optic zone 222. In the illustrated embodiment, second optical element 218 further includes a conductive tab 246 disposed adjacent to a periphery 248 of second optical element 218 and in electrically conductive communication with conductive layer 228. As shown in FIG. 2A, when first optical element 202 and second optical element 218 are coupled, such as through cooperative coupling of first alignment sidewall 204 and second alignment sidewall 220, second conductive tab 246 is in electrically conductive communication with conductive trace 296B and accordingly controller 232.

Still referring to FIGS. 2A-2C, first optical element 202 further includes a second mating blend zone 239 shaped to cooperatively couple with the second blend zone 242 when the first alignment sidewall 204 and the second alignment sidewall 220 are cooperatively coupled. Like mating blend zone 240A, second mating blend zone 239 is shaped to mirror the transition of second alignment sidewall 220 from second alignment sidewall ridge 244 to a surface 230 of second optic zone 222. In this regard, first optical element 202 and second optical element 218 are shaped to closely couple without second alignment sidewall ridge 244 contacting second blend zone 242.

In the illustrated embodiments, first optical element 202 and second optical element 218 are shown to include support tabs 284A-284C and 286A-286C, respectively. Such support tabs 284A-284C and 286A-286C are suitable support first optical element 202 and second optical element 218 such that conductive layers 216 and 228 respectively are not in contact with and/or scratched by a supporting surface (not shown), such as during a coating process or other manufacturing steps. Support tabs 284A-284C and 286A-286C are also suitable to rotationally align first optical element 202 and second optical element 218 relative to one another. Such yaw alignment is useful to align, for example, blend zone 208 and mating blend zone 240A. Yaw alignment may be further useful to align orientations of coatings disposed on the optical elements, as discussed further herein with respect to FIG. 4. In that regard, certain support tabs, shown here as support tabs 284C and 286B, include alignment slits 290 and 292, respectively. Such alignment slits 290 and 292 may also be used to rotationally align first optical element 202 and second optical element 218, such as during manufacturing and assembly. While alignment slits 290 and 292 are shown, it will be understood that other rotational alignment features, such alignment grooves or ridges (not shown), may be used to rotationally align first optical element 202 and second optical element 218, such as during manufacturing.

In an embodiment, ophthalmic device 200 further includes a third optical element 264 shaped to cooperatively couple with the second optical element 218. As discussed further herein with respect to FIGS. 3A-3C, such a third optical element 264 is suitable to define along with second optical element 218 a second cavity in which to dispose a second liquid crystal (not shown, see FIG. 4). Further, as discussed herein with respect to FIG. 4, such a third optical element 264 and liquid crystal disposed between the second optical element 218 and third optical element 264 may be suitable to provide polarization independence to the ophthalmic device 200.

As above, third optical element 264 and second optical element 218 are shaped to cooperatively couple. In that regard, second optical element 218 includes a third alignment sidewall 260 disposed about the second optic zone 222 and on a side of the second optical element 218 opposite the second alignment sidewall 220. Correspondingly, third optical element 264 includes a fourth alignment sidewall 266 disposed about a third optic zone 274 of the third optical element 264 and shaped to cooperatively couple with the third alignment sidewall 260. In this regard, the third alignment sidewall 260 and the fourth alignment sidewall 266 are shaped to align the second optical axis 226 of second optical element 218 and a third optical axis 268 of the third optical element 264. The third alignment sidewall 260 and the fourth alignment sidewall 266 are further shaped to define a second cavity (not shown, see FIG. 4) disposed between the second optical element 218 and the third optical element 264. As discussed further herein with respect to the first alignment sidewall 204 and the second alignment sidewall 220, the alignment of the second optical axis 226 and the third optical axis 268 is suitable to provide a clear optical image when mounted in or on an eye.

Ophthalmic device 200 is shaped to apply a voltage to a liquid crystal (not shown, see FIG. 4) disposed in the second cavity disposed between the second optical element 218 and the third optical element 264. As shown, the second optical element 218 further includes a third conductive layer 262 being optically transmissive disposed on a side of the second optical element 218 opposite the second alignment sidewall 220. Third optical element 264 includes a fourth conductive layer 272 being optically transmissive and disposed on the third optic zone 274 opposite the second optical element 218 facing the third conductive layer 262.

Further, the second optical element 218 includes a third blend zone shaped to transition the third alignment sidewall 260 shaped to a surface of the second optic zone 222 opposite the second alignment sidewall 220. Likewise, the third optical element 264 includes a fourth blend zone 279 shaped to transition the fourth alignment sidewall 266 from a ridge of the fourth alignment sidewall 266 to a surface 273 of the third optic zone 274 to form a pathway through the fourth alignment sidewall 266. The fourth conductive layer 272 is disposed on a surface 273 of the third optic zone 274 and on the fourth blend zone 279.

As shown, conductive trace 296C is in conductive communication with both controller 232 and the fourth conductive layer 272 disposed on the fourth blend zone 279, such that the fourth conductive layer 272 is positioned to receive electrical power from the controller 232. In that regard, in an embodiment, the controller 232 includes logic that when executed by the controller 232 causes the ophthalmic device 200 to perform operations comprising applying a voltage to the third conductive layer 262 and the fourth conductive layer 272, thereby changing an optical power of the ophthalmic device 200.

The second optical element 218 and the third optical element 264 each include mating blend zones 240B and 276, respectively, shaped to cooperatively couple with the blend zones 279 and 278 disposed on the third optical element 264 and the second optical element 218, respectively.

Figure 3A:
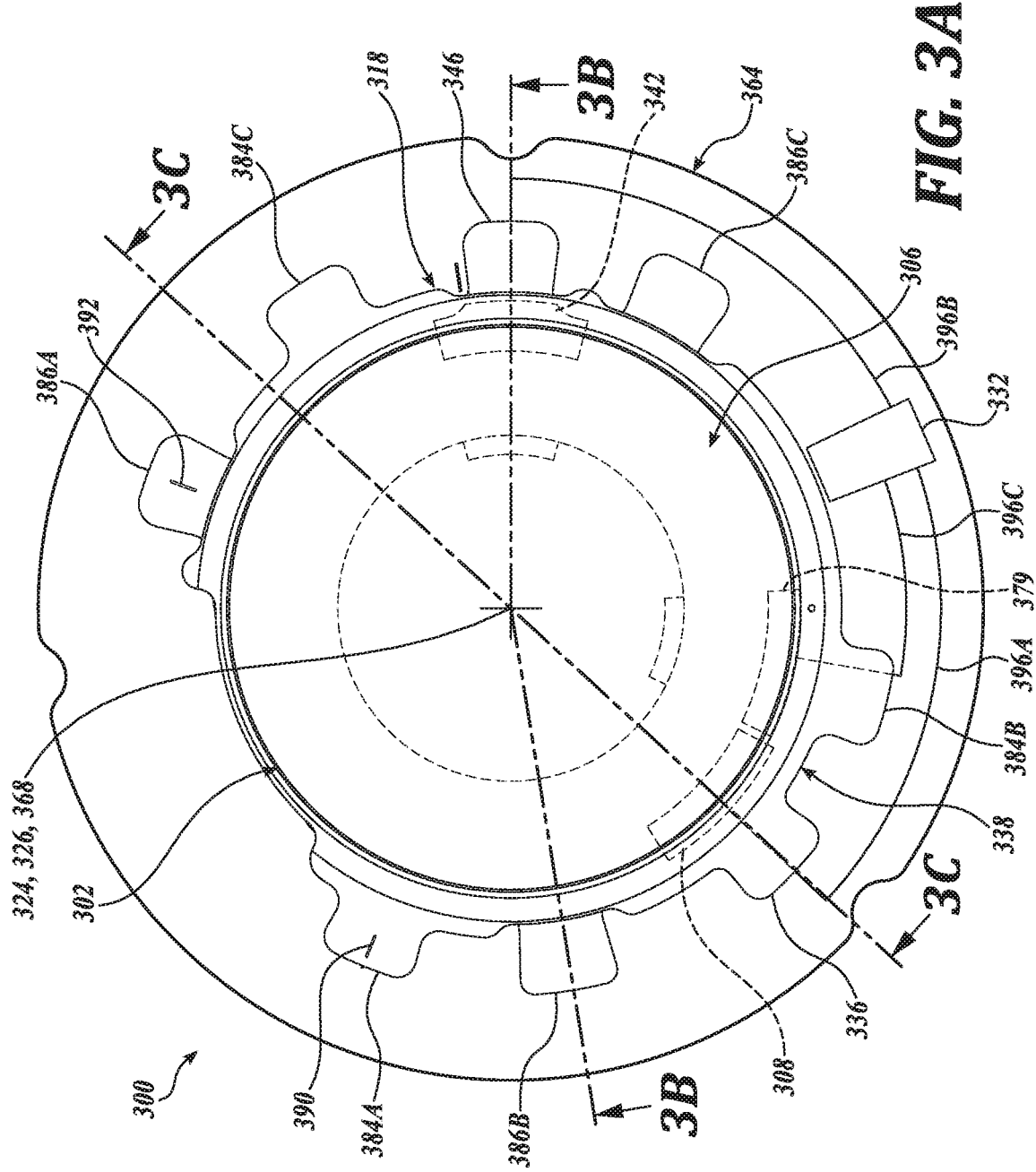
FIG. 3A is top-down plan view of an ophthalmic device, in accordance with an embodiment of the disclosure.
Figure 3B:
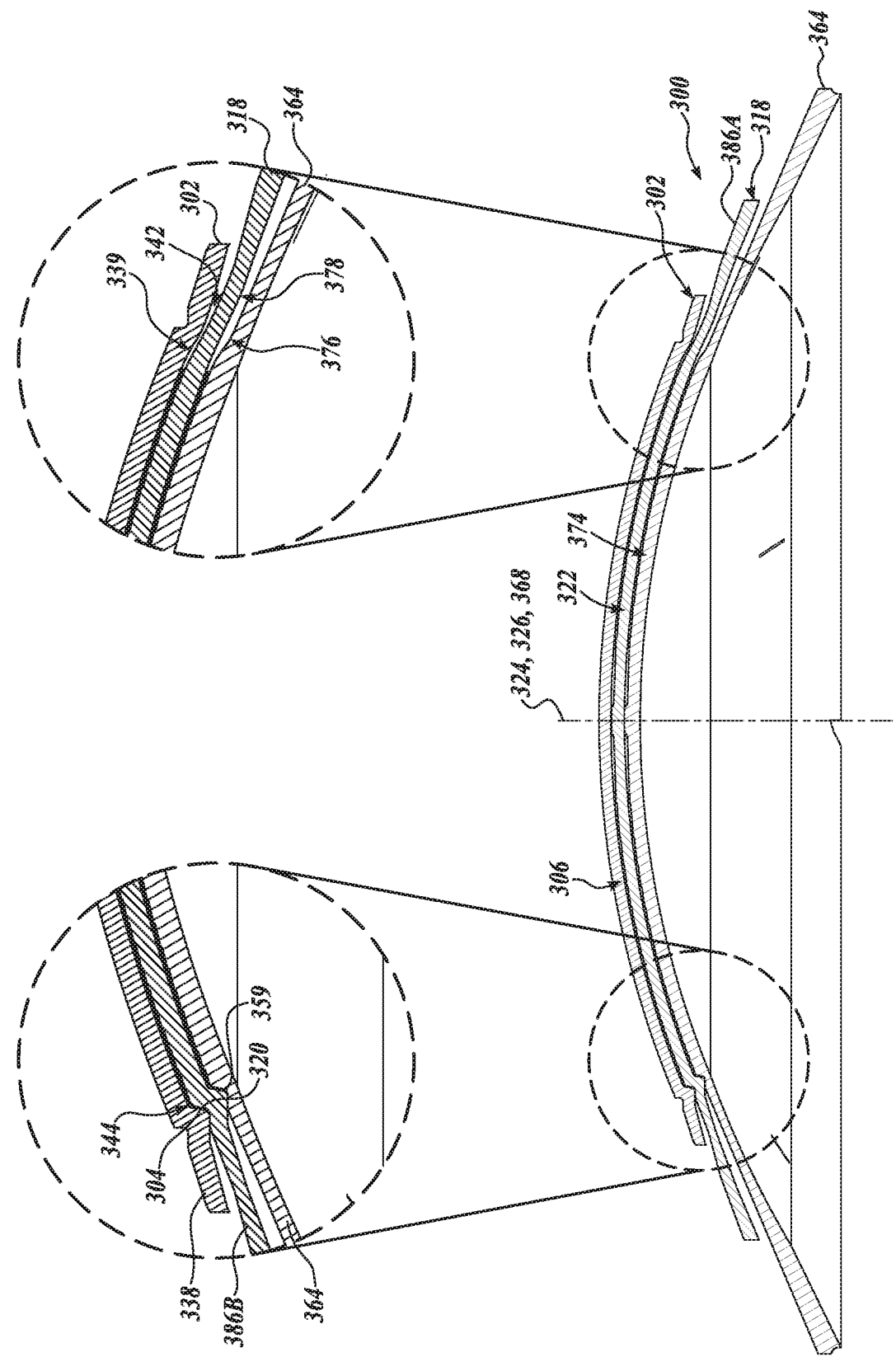
FIG. 3B is a view in cross-section of the ophthalmic device of FIG. 3A, in accordance with an embodiment of the disclosure.
Figure 3C:
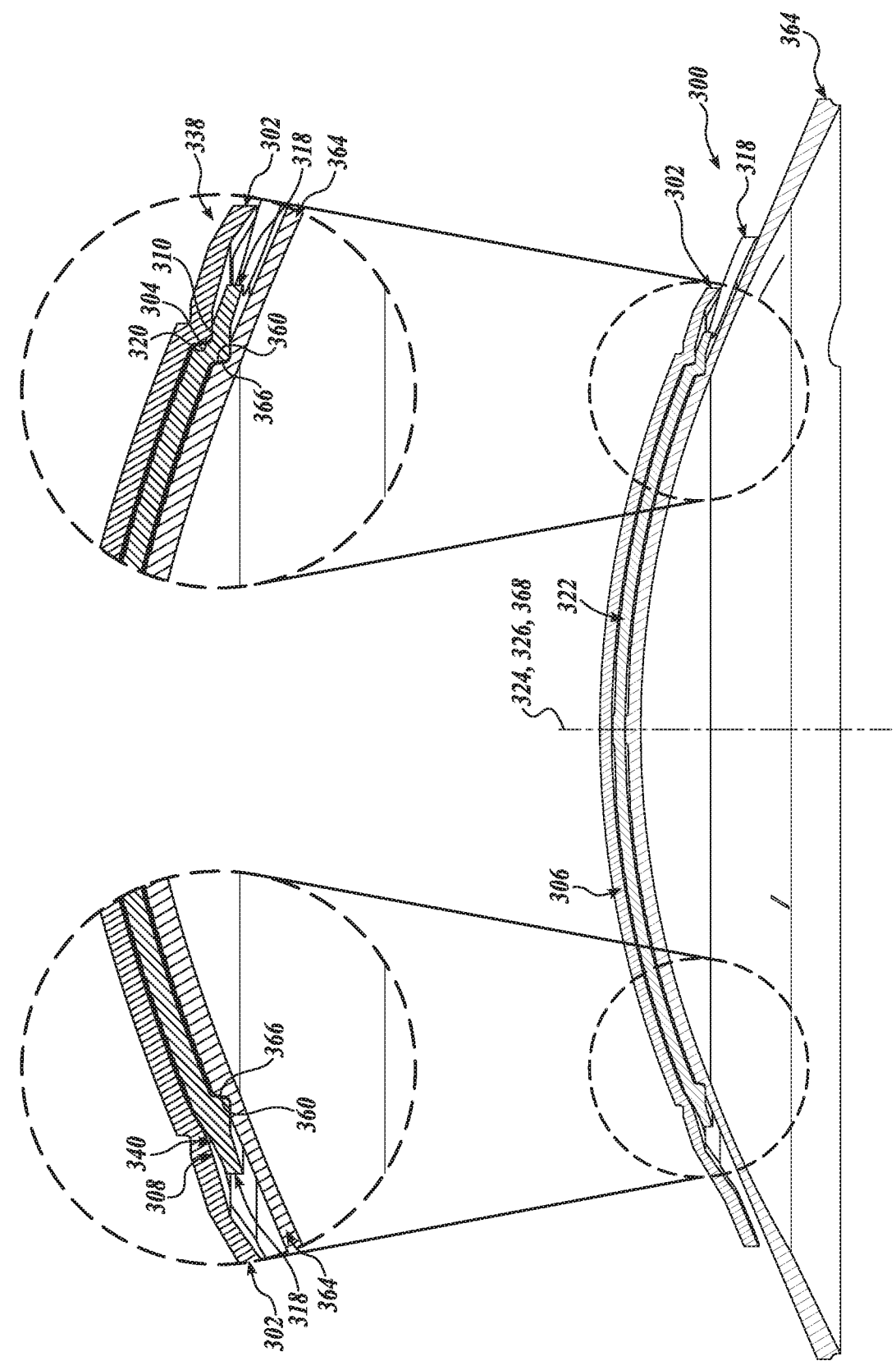
FIG. 3C is another view in cross-section of the ophthalmic device of FIG. 3A, in accordance with an embodiment of the disclosure.

FIG. 3A is top-down plan view of an ophthalmic device 300, in accordance with an embodiment of the disclosure. FIG. 3B is a view in cross-section of the ophthalmic device 300, in accordance with an embodiment of the disclosure. FIG. 3C is another view in cross-section of the ophthalmic device 300, in accordance with an embodiment of the disclosure. In an embodiment, ophthalmic device 300 is an example of ophthalmic device 200.

Ophthalmic device 300 is shown to include first optical element 302, second optical element 318, and third optical element 364. In an embodiment, first optical element 302 is an example of optical element 102.

First optical element 302 includes first alignment sidewall 304 and second optical element 318 includes alignment sidewall 320. As illustrated in FIG. 3B, first and second alignment sidewalls 304 and 320 are shaped to cooperatively couple. In the illustrated embodiment, second alignment sidewall 320 is shaped to nest within first alignment sidewall 304. See FIG. 3B, left, FIG. 3C, right. In this regard, central optical axis 324 of first optical element 302 and central optical axis 326 are aligned when first alignment sidewall 304 and second alignment sidewall 320 are cooperatively coupled.

First optical element 302 further includes support tabs 384A-384C and second optical element 318 further includes support tabs 386A-386C. As discussed further herein with respect to FIGS. 2A-2C, such support tabs are suitable to protect conductive layers from scratching and to align first optical element 302 and second optical element 318 with respect to one another and with respect to third optical element 364. Alignment slits 390 and 392, such as vias, are suitable for such alignment, such as during assembly and manufacturing of ophthalmic device 300. As discussed further herein with respect to FIGS. 2A-2C, while alignment slits 390 and 392 are shown, other alignment features, such as alignment grooves or ridges (not shown), may be included.

Second optical element 318 further includes third alignment sidewall 360 disposed on a side of second optical element 318 opposite alignment sidewall 320 and facing third optical element 364. Correspondingly, third optical element 364 includes fourth alignment sidewall 366 shaped to cooperatively couple with third alignment sidewall 360 disposed about third optic zone 374. As shown, central optical axis 326 optical second optical element 318 and central optical axis 368 of third optical element 364 are aligned when third alignment sidewall 360 and fourth alignment sidewall 366 are cooperatively coupled. Further, fourth alignment sidewall 366 is shaped to nest within third alignment sidewall 360.

First optical element 302 includes blend zone 308 disposed in the first alignment sidewall 304 and shaped to transition the first alignment sidewall 304 from a ridge 310 of the first alignment sidewall 304 to a surface of the first optic zone 306. In this regard, blend zone 308 forms a pathway through the first alignment sidewall 304, as shown in FIG. 3C, left. As shown, blend zone 308 is curvature continuous with a surface of the first optic zone 306 of first optical element 302. In an embodiment, the blend zone 308 is smooth, but not necessarily curvature continuous with a surface of the first optic zone 306. Correspondingly, second optical element 318 includes a mating blend zone 340 shaped to cooperatively couple with the blend zone 308 when the first alignment sidewall 304 and the second alignment sidewall 320 are cooperatively coupled. In this regard, a conductive layer disposed on the first optical element 302 (not shown, see FIG. 4) may be placed in electrically conductive communication with controller 332, such as through conductive trace 396A, when the first alignment sidewall 304 and the second alignment sidewall 320 are cooperatively coupled and the third alignment sidewall 360 and the fourth alignment sidewall 366 are cooperatively coupled.

The blend zone 308 of the first optical element 302 and the mating blend zone 340 of the second optical element 318, as in illustrated in FIG. 3C, left, are in contrast to portions of the ophthalmic device 300 in which the first alignment sidewall 304 and the second alignment sidewall 320 are cooperatively coupled. For example, as illustrated in FIG. 3C, right, where first alignment sidewall 304 and second alignment sidewall 320 are cooperatively coupled there is no pathway from a periphery 338 of the first optical element 302 to the optic zone 306 of the first optical element 302.

As shown in FIG. 3B, second optical element 318 includes second blend zone 342 disposed in the second alignment sidewall 320 and shaped to transition the second alignment sidewall 320 from a ridge 344 of the second alignment sidewall 320 to a surface of the second optic zone 322. In this regard, the second blend zone 342 forms a pathway through the second alignment sidewall 320, and wherein the second conductive layer (not shown, see FIG. 4) is disposed on and extending through the pathway of the second blend zone 342 and disposed on the second optic zone 322. See FIG. 3B, right. Second blend zone 342 is disposed on a first side of second optical element 318 and positioned to face first optical element 302 when first alignment sidewall 304 and second alignment sidewall 320 are cooperatively coupled. Additionally, first optical element 302 includes mating blend zone 339 shaped to cooperatively couple with the second blend zone 342 when the first alignment sidewall 304 and the second alignment sidewall 320 are cooperatively coupled and allow such coupling of first optical element 302 and second optical element 318 without the second blend zone 342 and a portion of the first alignment sidewall 304 contacting.

Second optical element 318 further includes third blend zone 378 shaped to transition the third alignment sidewall 360 from a ridge 359 of the third alignment sidewall 360 to a surface of the second optic zone 322 to form a pathway through the third alignment sidewall 360. Third optical element 364 includes a third mating blend zone 376 shaped to cooperatively couple with the third blend zone 378 when the third alignment sidewall 360 and the fourth alignment sidewall 366 are cooperatively coupled. Third optical element 364 further includes fourth blend zone 379 having a fourth conductive layer (not shown, see FIG. 4) disposed thereon and in conductive communication with conductive trace 396C and controller 332 through conductive trace 396C.

In the illustrated embodiment, the second blend zone 342 and third blend zone 378 are vertically stacked or aligned with respect to second optical axis 326. See FIG. 3B, right. In this regard and as shown, conductive layers (not shown, see FIG. 4) are both in electrically conductive communication with and adjacent to second conductive tab 346 and controller 332 through conductive trace 396B. In another embodiment the second blend zone 342 is in electrically conductive communication with second conductive tab 346 and third blend zone 378 is in electrically conductive communication with a third conductive tab (not shown), where second blend zone 342 and third blend zone 378 are not vertically aligned.

As shown, where blend zones and mating blend zones meet, such as first blend zone 308 and mating blend zone 340, a gap or capillary is defined by adjacent, coupled optical elements, such as first optical element 302 and second optical element 318. Such a gap or capillary provides a pathway to a cavity defined by the first optical element 302 and the second optical element 318 (not shown, see FIG. 4). The gap or capillary is shaped to retain a liquid crystal (not shown, See FIG. 4) disposed in the cavity such as through capillary forces. The gap or capillary may also be used to fill the cavity such as through injection of the liquid crystal through the gap or capillary.

Figure 4:
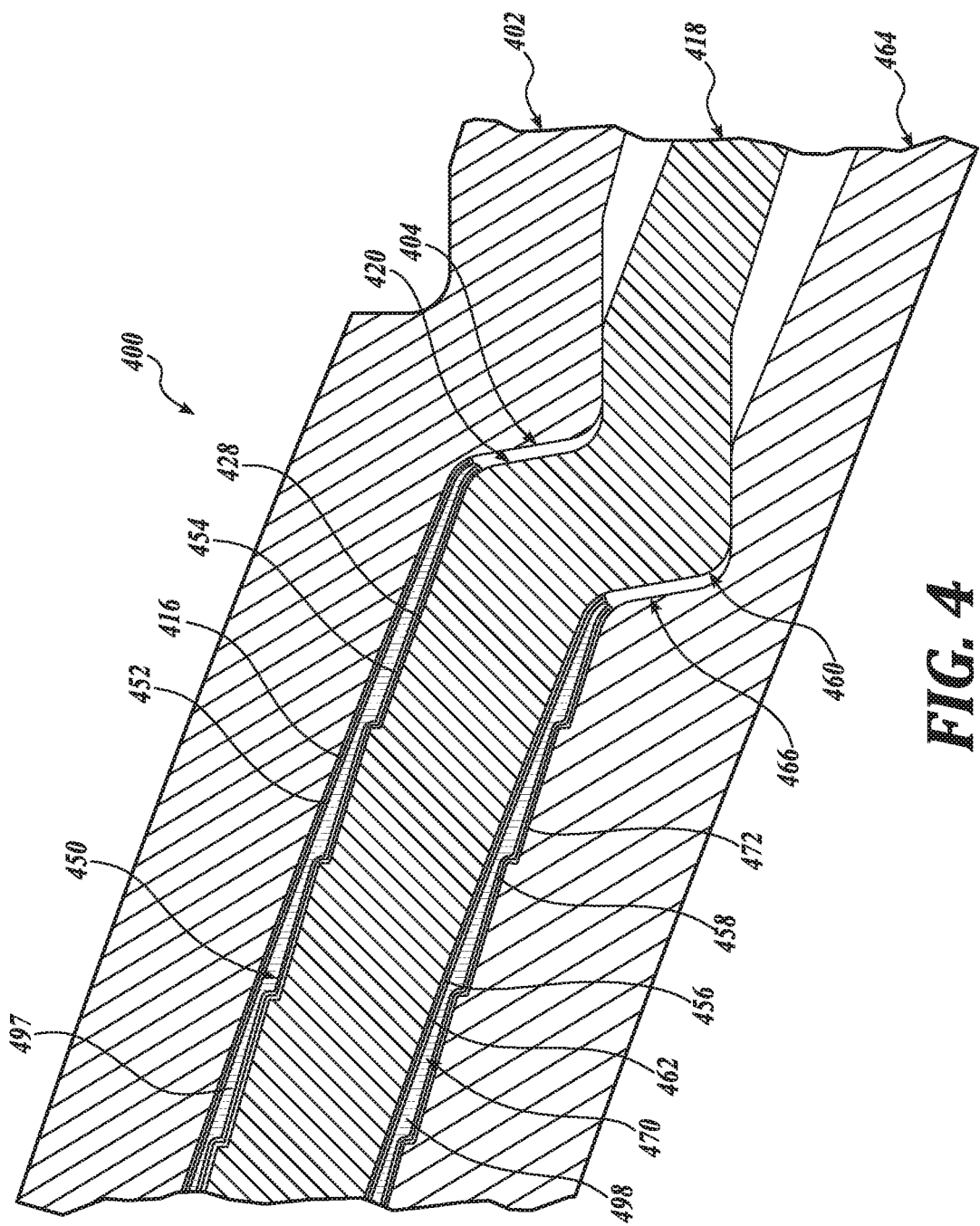
FIG. 4 is a partial view in cross-section of an ophthalmic device, in accordance with an embodiment of the disclosure.

FIG. 4 is a partial view in cross-section of on ophthalmic device 400, in accordance with an embodiment of the disclosure. As shown, ophthalmic device 400 includes first optical element 402, second optical element 418, and third optical element 464. In an embodiment, ophthalmic device 400 is an example of ophthalmic devices 200 and/or 300. In an embodiment, first optical element 402 is an example of optical element 102.

In the illustrated embodiment, fist optical element 402 includes first alignment sidewall 404 shaped to cooperatively couple with second alignment sidewall 420 of second optical element 418. Likewise, second optical element 418 includes third alignment sidewall 460 shaped to cooperatively couple with fourth alignment sidewall 466 of third optical element 464. As discussed further herein with respect to FIGS. 2A-2C and 3A-3C, such cooperative coupling of first alignment sidewall 404 with second alignment sidewall 420 and third alignment sidewall 460 with fourth alignment sidewall 466 aligns optical axes (not shown, see FIGS. 3A-3C) of the first optical element 402 and second optical element 418 and the second optical element 418 and the third optical element 464, respectively. As shown, the fourth alignment sidewall 466 is nested within the third alignment sidewall 460 and the second alignment sidewall 420 is nested within the first alignment sidewall 404.

The illustrated portion of ophthalmic device 400 shows the alignment sidewalls of first optical element 402, second optical element 418, and third optical element 464 cooperatively coupled. However, it will be understood that, in certain embodiments, the optical elements 402, 418, and 464 of ophthalmic device 400 include one or more blend zones and mating blend zones, as discussed further herein with respect to FIGS. 1, 2A-2C, and 3A-3C.

As shown, first optical element 402 and second optical element 418 include first conductive layer 416 and second conductive layer 428, respectively. In the illustrated embodiment, first conductive layer 416 and second conductive layer 428 are positioned to face each other when first alignment sidewall 404 and second alignment sidewall 420 are cooperatively coupled. Further, first optical element 402 includes first insulating layer 452 disposed on the first conductive layer 416 and second optical element 418 includes second insulating layer 454 disposed on the second conductive layer 428. The first insulating layer 452 and second insulating layer 454 are shaped to electrically isolate the first conductive layer 416 from the second conductive layer 428, such as by covering or encapsulating the first conductive layer 416 and the second conductive layer 428.

First optical element 402 and second optical element 418 are shaped to define a cavity 450 disposed between the first optical element 402 and the second optical element 418 when the first alignment sidewall 404 and the second alignment sidewall 420 are cooperatively coupled. In an embodiment, ophthalmic device 400 includes a first liquid crystal 497 disposed in cavity 450. As discussed further herein, by applying a voltage to first conductive layer 416 and second conductive layer 428, a refractive index of the first liquid crystal 497 is changed, thereby changing an optical power of ophthalmic device 400.

In the illustrated embodiment, second optical element 418 and third optical element 464 are shaped to define a second cavity 470 disposed between the second optical element 418 and the third optical element 464 when third alignment sidewall 460 and fourth alignment sidewall 466 are cooperatively coupled. In an embodiment, ophthalmic device 400 includes a second liquid crystal 498 disposed in the second cavity 470.

Likewise, second optical element 418 includes a third conductive layer 462 being optically transmissive disposed on a side of the second optical element 418 opposite the second alignment sidewall 420 and a third insulating layer 456 disposed on the third conductive layer 462. Third optical element 464 includes a fourth conductive layer 472 being optically transmissive disposed opposite the second optical element 418 and a fourth insulating layer 458 disposed on the fourth conductive layer 472. The third insulating layer 456 and the fourth insulating layer 458 are shaped to electrically isolate the third conductive layer 462 from the fourth conductive layer 472, such as by covering or encapsulating the third conductive layer 462 and the fourth conductive layer 472, respectively. In this regard, ophthalmic device 400 is configured to apply a voltage to third conductive layer 462 and fourth conductive layer 472 and apply an electrical bias to second liquid crystal 498 in the second cavity 470, thereby changing a refractive index to the second liquid crystal 498 and an optical power of ophthalmic device 400.

In an embodiment, the insulating layers 452, 454, 456, and 458 are shaped to align molecules of liquid crystals 497 and 498 in contact with surfaces of the insulating layers 452, 454, 456, and 458. In an embodiment, insulating layers 452 and 454 are shaped to align first liquid crystal 497 disposed in the first cavity 450 in a first direction and insulating layers 456 and 458 are shaped to align molecules of second liquid crystal 498 disposed in the second cavity 470 in a second direction orthogonal to the first direction. In this regard, the ophthalmic device 400 is configured to provide polarization independence and avoid producing, for example, a blurred image superimposed on a sharp image. The orthogonality of the insulating layers 452 and 454 with respect to insulating layers 456 and 458 may be achieved by orientation of the optical elements 402, 418, and 464 with respect to one another, such as with alignment slits (not shown, see FIGS. 2A-2C).

Figure 5:
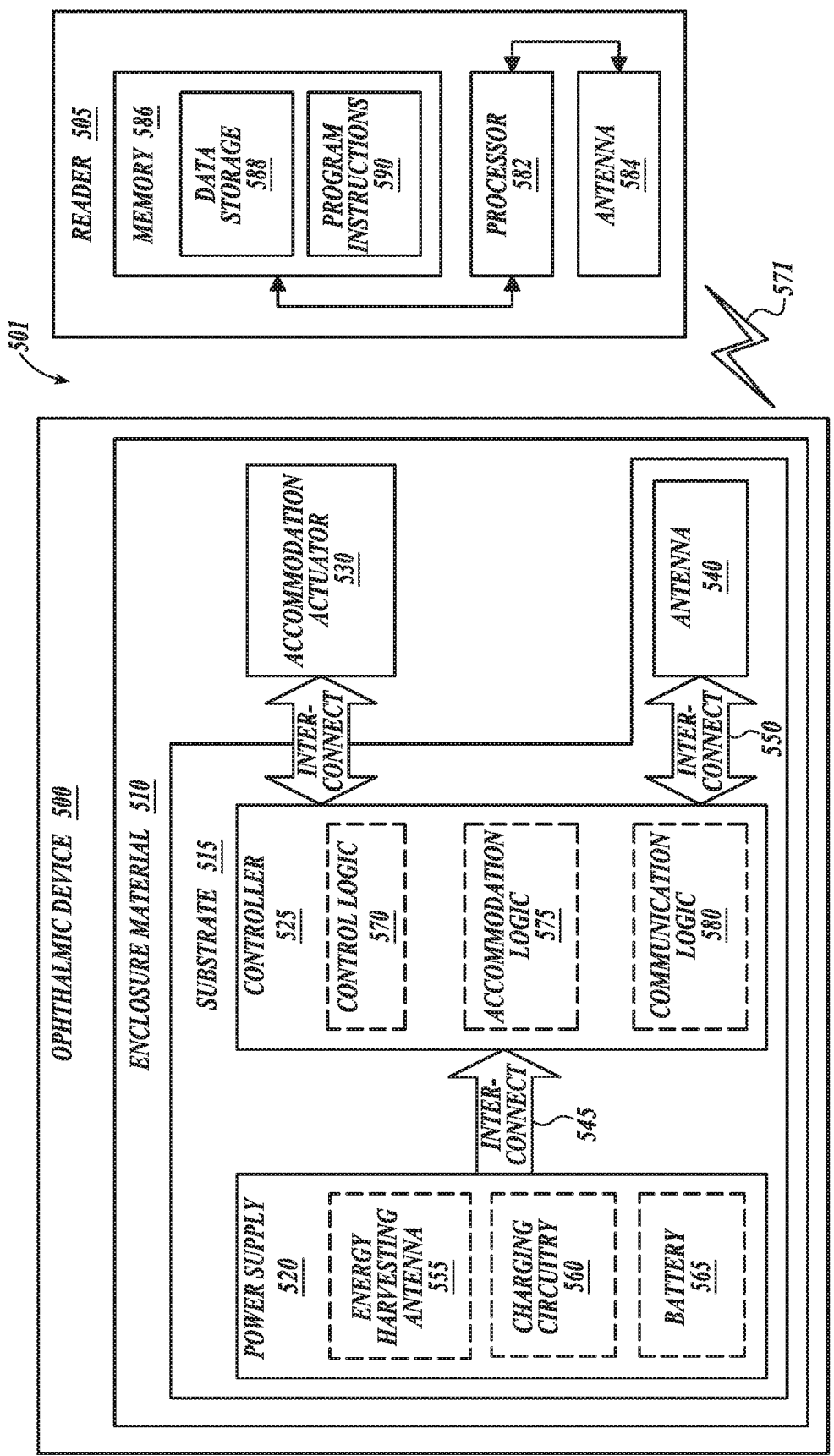
FIG. 5 is a functional block diagram of an ophthalmic device, in accordance with an embodiment of the present disclosure.

FIG. 5 is a functional block diagram of an ophthalmic system 501 including an ophthalmic device 500 including alignment sidewalls and blend zones in accordance with an embodiment of the present disclosure. In an embodiment, ophthalmic device 500 is an example of ophthalmic devices 200, 300, and/or 400. Ophthalmic device 500 may be an on-eye device, such as a contact lens or a smart contact lens, or an implantable device, such as an intraocular lens. In the depicted embodiment, ophthalmic device 500 includes an enclosure material 510 formed to be either contact-mounted to a corneal surface of an eye or implanted into an eye. A substrate 515 is embedded within or surrounded by enclosure material 510 to provide a mounting surface for a power supply 520, a controller 525, an antenna 540, and various interconnects 545 and 550. The substrate 515 and the associated electronics may be one implementation of the controller 232 and/or controller 332. The illustrated embodiment of power supply 520 includes an energy harvesting antenna 555, charging circuitry 560, and a battery 565. The illustrated embodiment of controller 525 includes control logic 570, accommodation logic 575, and communication logic 580. As shown, accommodation actuator 530 is disposed in the enclosure material 510.

Power supply 520 supplies operating voltages to the controller 525 and/or the accommodation actuator 530. Antenna 540 is operated by the controller 525 to communicate information to and/or from ophthalmic device 500. In the illustrated embodiment, antenna 540, controller 525, and power supply 520 are disposed on/in substrate 515, while accommodation actuator 530 is disposed in enclosure material 510 (not in/on substrate 515). However, in other embodiments, the various pieces of circuitry and devices contained in ophthalmic device 500 may be disposed in/on substrate 515 or in enclosure material 510, depending on the specific design of ophthalmic device 500. For example, in one embodiment, accommodation actuator 530 may be disposed on a transparent substrate.

Substrate 515 includes one or more surfaces suitable for mounting controller 525, power supply 520, and antenna 540. Substrate 515 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide or silver nanowire mesh) can be patterned on substrate 515 to form circuitry, electrodes, etc. For example, antenna 540 can be formed by depositing a pattern of gold or another conductive material on substrate 515. Similarly, interconnects 545 and 550 can be formed by depositing suitable patterns of conductive materials on substrate 515. A combination of resists, masks, and deposition techniques can be employed to pattern materials on substrate 515. Substrate 515 can be a relatively rigid material, such as polyethylene terephthalate ("PET") or another material sufficient to structurally support the circuitry and/or electronics within enclosure material 510. Ophthalmic device 500 can alternatively be arranged with a group of unconnected substrates rather than a single substrate 515. For example, controller 525 and power supply 520 can be mounted to one substrate 515, while antenna 540 is mounted to another substrate 515 and the two can be electrically connected via interconnects. Substrate 515 may also be a continuous piece of semiconductor, housing all or some of the aforementioned pieces of device architecture as integrated circuitry.

Substrate 515 can be shaped as a flattened ring with a radial width dimension sufficient to provide a mounting platform for the embedded electronic components. Substrate 515 can have a thickness sufficiently small to allow substrate 515 to be embedded in enclosure material 510 without adversely influencing the profile of ophthalmic device 500. Substrate 515 can have a thickness sufficiently large to provide structural stability suitable for supporting the electronics mounted thereon. For example, substrate 515 can be shaped as a ring with a diameter of about 10 millimeters, a radial width of about 1 millimeter (e.g., an outer radius 1 millimeter larger than an inner radius), and a thickness of about 50 micrometers. Substrate 515 can optionally be aligned with the curvature of the eye-mounting surface of ophthalmic device 500 (e.g., convex surface). For example, substrate 515 can be shaped along the surface of an imaginary cone between two circular segments that define an inner radius and an outer radius. In such an example, the surface of substrate 515 along the surface of the imaginary cone defines an inclined surface that is approximately aligned with the curvature of the eye mounting surface at that radius.

In the illustrated embodiment, power supply 520 includes a battery 565 to power the various embedded electronics, including controller 525. Battery 565 may be inductively charged by charging circuitry 560 and energy harvesting antenna 555. In one embodiment, antenna 540 and energy harvesting antenna 555 are independent antennae, which serve their respective functions of energy harvesting and communications. In another embodiment, energy harvesting antenna 555 and antenna 540 are the same physical antenna that are time shared for their respective functions of inductive charging and wireless communications with reader 505. Additionally or alternatively, power supply 520 may include a solar cell ("photovoltaic cell") to capture energy from incoming ultraviolet, visible, and/or infrared radiation. Furthermore, an inertial power scavenging system can be included to capture energy from ambient vibrations.

Charging circuitry 560 may include a rectifier/regulator to condition the captured energy for charging battery 565 or directly power controller 525 without battery 565. Charging circuitry 560 may also include one or more energy storage devices to mitigate high frequency variations in energy harvesting antenna 555. For example, one or more energy storage devices (e.g., a capacitor, an inductor, etc.) can be connected to function as a low-pass filter.

Controller 525 contains logic to choreograph the operation of the other embedded components. Control logic 570 controls the general operation of ophthalmic device 500, including providing a logical user interface, power control functionality, etc. Accommodation logic 575 includes logic for receiving signals from sensors monitoring the orientation of the eye, determining the current gaze direction or focal distance of the user, and manipulating accommodation actuator 530 (focal distance of the contact lens) in response to these physical cues. The auto-accommodation can be implemented in real-time based upon feedback from gaze tracking, or permit the user to select specific accommodation regimes (e.g., near-field accommodation for reading, far-field accommodation for regular activities, etc.). Communication logic 580 provides communication protocols for wireless communication with reader 505 via antenna 540. In one embodiment, communication logic 580 provides backscatter communication via antenna 540 when in the presence of an electromagnetic field 571 output from reader 505. In one embodiment, communication logic 580 operates as a smart wireless radio-frequency identification ("RFID") tag that modulates the impedance of antenna 540 for backscatter wireless communications. The various logic modules of controller 525 may be implemented in software/firmware executed on a general purpose microprocessor, in hardware (e.g., application specific integrated circuit), or a combination of both.

Ophthalmic device 500 may include various other embedded electronics and logic modules. For example, a light source or pixel array may be included to provide visible feedback to the user. An accelerometer or gyroscope may be included to provide positional, rotational, directional or acceleration feedback information to controller 525.

The illustrated embodiment also includes reader 505 with a processor 582, an antenna 584, and memory 586. Memory 586 in reader 505 includes data storage 588 and program instructions 590. As shown reader 505 may be disposed outside of ophthalmic device 500, but may be placed in its proximity to charge ophthalmic device 500, send instructions to ophthalmic device 500, and/or extract data from ophthalmic device 500. In one embodiment, reader 505 may resemble a conventional contact lens holder that the user places ophthalmic device 500 in at night to charge, extract data, clean the lens, etc.

External reader 505 includes an antenna 584 (or group of more than one antennae) to send and receive wireless signals 571 to and from ophthalmic device 500. External reader 505 also includes a computing system with a processor 582 in communication with a memory 586. Memory 586 is a non-transitory computer-readable medium that can include, without limitation, magnetic disks, optical disks, organic memory, and/or any other volatile (e.g., RAM) or non-volatile (e.g., ROM) storage system readable by the processor 182. Memory 586 can include a data storage 588 to store indications of data, such as data logs (e.g., user logs), program settings (e.g., to adjust behavior of ophthalmic device 500 and/or external reader 505), etc. Memory 586 can also include program instructions 590 for execution by processor 582 to cause the external reader 505 to perform processes specified by the instructions 590. For example, program instructions 590 can cause external reader 505 to provide a user interface that allows for retrieving information communicated from ophthalmic device 500 or allows transmitting information to ophthalmic device 500 to program or otherwise select operational modes of ophthalmic device 500. External reader 505 can also include one or more hardware components for operating antenna 584 to send and receive wireless signals 571 to and from ophthalmic device 500.

External reader 505 can be a smart phone, digital assistant, or other portable computing device with wireless connectivity sufficient to provide the wireless communication link 571. External reader 505 can also be implemented as an antenna module that can be plugged into a portable computing device, such as in an embodiment where the communication link 571 operates at carrier frequencies not commonly employed in portable computing devices. In some instances, external reader 505 is a special-purpose device configured to be worn relatively near a wearer's eye to allow the wireless communication link 571 to operate with a low power budget. For example, the external reader 505 can be integrated in a piece of jewelry such as a necklace, earing, etc. or integrated in an article of clothing worn near the head, such as a hat, headband, etc.

In another aspect, the present disclosure provides a method 600 for assembling an ophthalmic device. In an embodiment, the method includes aligning a blend zone disposed in an alignment sidewall of a first optical element shaped to transition the first alignment sidewall from a ridge of the first alignment sidewall to a surface of a first optic zone of the first optical element to form a pathway through the first alignment sidewall with a mating blend zone disposed in an alignment sidewall of a second optical element shaped to cooperatively couple with the blend zone; and cooperatively coupling the alignment sidewall of the first optical element with the alignment sidewall of the second optical element to align an optical axis of the first optical element with an optical axis of the second optical element. As discussed further herein, by cooperatively coupling the first alignment sidewall and the second alignment sidewall, a conductive layer disposed on the optic zone and being optically transmissive may be placed in conductive communication with a power such suitable to provide signals and power to the conductive layer.

Figure 6:
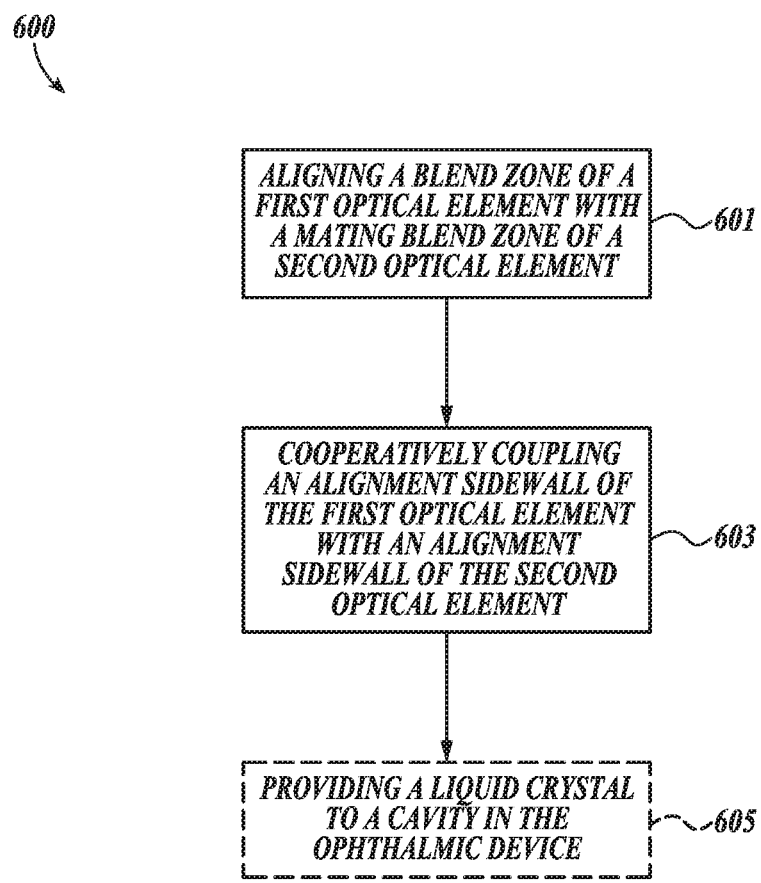
FIG. 6 is a block diagram of a method of assembling an ophthalmic device, in accordance with an embodiment of the disclosure.

FIG. 6 illustrates an example of method 600. The method may be used to form ophthalmic devices 200, 300, 400, and 500.

As shown, method 600 can begin with process block 601 including aligning a blend zone disposed in a sidewall of a first optical element with a mating blend zone disposed in an alignment sidewall of a second optical element. In an embodiment, the blend zone is disposed in an alignment sidewall of a first optical element shaped to transition the first alignment sidewall from a ridge of the first alignment sidewall to a surface of a the first optic zone of the first optical element to form a pathway through the first alignment sidewall. See, for example, FIG. 1. Further, in an embodiment, mating blend zone disposed in an alignment sidewall of a second optical element shaped to cooperatively couple with the blend zone. Such a mating blend zone may be disposed in an alignment sidewall of a second optical element shaped to transition the second alignment sidewall from a ridge of the second alignment sidewall to a surface of a second optic zone of the second optical element. See for example, FIG. 2B and FIG. 3B.

Method 600 may begin with process block 601, which includes aligning a blend zone of the first optical element with mating blend zone of the second optical element. In this regard, the first optical element and the second optical element may be cooperatively coupled without contacting, for example, an alignment sidewall of the second optical element with the blend zone of the first optical element and/or an alignment sidewall of the first optical element with the mating blend zone. As discussed further herein with respect to FIGS. 2A-2C, such rotational alignment may be accomplished using support tabs disposed on the first and second optical elements and/or with alignment slots disposed in the support tabs.

Process block 601 may be followed by process block 603, which includes cooperatively coupling an alignment sidewall of the first optical element with an alignment sidewall of the second optical element. In this regard, an optical axis of the first optical element is aligned with an optical axis of the second optical element. As discussed further herein with respect to, for example, FIGS. 2A-2C and 3A-3C, such alignment of optical axes of the first and second optical elements provides a clear image, such as when mounted in or on an eye. Such cooperative coupling may include pressing an inner surface of the first alignment sidewall into an outer surface of the second alignment sidewall such that, for example, the second alignment sidewall nests within the first alignment sidewall.

In an embodiment, cooperatively coupling the first alignment sidewall with the second alignment sidewall places a conductive layer disposed on the optic zone and being optically transmissive in conductive communication with a power source through the pathway of the blend zone. As discussed further herein with respect to FIGS. 2A-2C, such conductive communication between the conductive layer and the power source is suitable to provide electrical power and signals to the conductive layer. By providing such electrical power to the conductive layers, a refractive index of liquid crystals disposed in the ophthalmic device may be changed and, accordingly, an optical power of the ophthalmic device.

Process block 603 may be followed by process block 605, which includes providing a liquid crystal to the ophthalmic device. In an embodiment, the first optical element and the second optical element define a cavity disposed between the first optical element and the second optical element when the first alignment sidewall and the second alignment sidewall are cooperatively coupled. See, for example, FIG. 4. In an embodiment, providing the liquid crystal to the ophthalmic device includes injecting or otherwise providing the liquid crystal through a gap defined by the blend zone and the mating blend zone and into the cavity, such as after process block 603 and as shown in FIG. 6. In an embodiment, the liquid crystal is held in the cavity at least in part due to capillary forces between the gap and the liquid crystal.

In another embodiment, providing the liquid crystal includes providing the liquid crystal onto a surface of the first optic zone of the first optical element or the second optic zone of the second optical element. In an embodiment, providing the liquid crystal onto a surface of the optic zone of the first optical element or the second optical element occurs before cooperatively coupling the alignment sidewall of the first optical element and the alignment sidewall of the second optical element. As liquid crystal is provided to the optical zone, the liquid crystal tends to adhere to and trace the portions of the optic zone adjacent to the ridge of the alignment sidewall. Further, the liquid crystal tends not to enter the pathway of the blend zone until the optic zone has filled with liquid crystal. In this regard, the optic zone tends to be free of bubbles or free space not filled with liquid crystal due to the pathway of the blend zone. Accordingly, when the first optical element and second optical element are cooperatively coupled, the cavity disposed therebetween tends to be free of bubbles and to be filled instead with liquid crystal.

The order in which some or all of the process blocks appear in each process should not be deemed limiting. Rather, one of ordinary skill in the art having the benefit of the present disclosure will understand that some of the process blocks may be executed in a variety of orders not illustrated, or even in parallel.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An ophthalmic device comprising:
    a first optical element comprising:
        a first alignment sidewall disposed about a first optic zone of the first optical element;
        a blend zone disposed in the first alignment sidewall and shaped to transition the first alignment sidewall from a ridge of the first alignment sidewall to a surface of the first optic zone to form a pathway through the first alignment sidewall; and
        a first conductive layer being optically transmissive disposed on the surface of the first optic zone and extending through the pathway of the blend zone; and
    a second optical element comprising:
        a second alignment sidewall disposed about a second optic zone of the second optical element and shaped to cooperatively couple with the first alignment sidewall to align a first optical axis of the first optical element with a second optical axis of the second optical element.

2. The ophthalmic device of claim 1, further comprising a second conductive layer being optically transmissive disposed on a surface of the second optic zone facing the first optical element.

3. The ophthalmic device of claim 2, further comprising a controller comprising logic that when executed by the controller causes the ophthalmic device to perform operations comprising:
applying a voltage to the first conductive layer and the second conductive layer, thereby changing an optical power of the ophthalmic device.

4. The ophthalmic device of claim 1, wherein the blend zone is rotationally asymmetric with respect to the first optical axis.

5. The ophthalmic device of claim 1, wherein a central portion of the blend zone is curvature continuous with a curvature of the first optic zone.

6. The ophthalmic device of claim 1, wherein the first optical element further comprises a first conductive tab disposed at a periphery of the first optical element in electrically conductive communication with the first conductive layer.

7. The ophthalmic device of claim 1, wherein the second optical element comprises a mating blend zone shaped to cooperatively couple with the blend zone when the first alignment sidewall and the second alignment sidewall are cooperatively coupled.

8. The ophthalmic device of claim 7, wherein the blend zone has an arc length relative to the first optical axis, and wherein the mating blend zone has an arc length relative to the second optical axis that is different than the arc length of the blend zone.

9. The ophthalmic device of claim 1, wherein the first alignment sidewall has an angle relative to the first optical axis in a range of about 2° to about 15°.

10. The ophthalmic device of claim 1, wherein the second alignment sidewall is shaped to nest within the first alignment sidewall when the first alignment sidewall and the second alignment sidewall are cooperatively coupled.

11. The ophthalmic device of claim 2, wherein the second optical element further comprises a second blend zone disposed in the second alignment sidewall and shaped to transition the second alignment sidewall from a ridge of the second alignment sidewall to a surface of the second optic zone to form a pathway through the second alignment sidewall, and wherein the second conductive layer is disposed on and extending through the pathway of the second blend zone and disposed on the second optic zone.

12. The ophthalmic device of claim 11, wherein the first optical element further comprises a second mating blend zone shaped to cooperatively couple with the second blend zone when the first alignment sidewall and the second alignment sidewall are cooperatively coupled.

13. The ophthalmic device of claim 11, wherein the second optical element further comprises a second conductive tab disposed at a periphery of the second optical element in electrically conductive communication with the second conductive layer.

14. The ophthalmic device of claim 1, wherein the first optical element and the second optical element define a cavity disposed between the first optical element and the second optical element when the first alignment sidewall and the second alignment sidewall are cooperatively coupled.

15. The ophthalmic device of claim 14, further comprising a liquid crystal disposed in the cavity.

16. The ophthalmic device of claim 2, further comprising a first insulating layer disposed on the first conductive layer and a second insulating layer disposed on the second conductive layer, wherein the first insulating layer and the second insulating layer are shaped to electrically isolate the first conductive layer from the second conductive layer.

17. The ophthalmic device of claim 14, further comprising a third optical element shaped to couple with the second optical element to define a second cavity disposed between the second optical element and the third optical element.

18. A method of assembling an ophthalmic device comprising:
aligning a blend zone disposed in a first alignment sidewall of a first optical element shaped to transition the first alignment sidewall from a ridge of the first alignment sidewall to a surface of a first optic zone of the first optical element to form a pathway through the first alignment sidewall with a mating blend zone disposed in a second alignment sidewall of a second optical element shaped to transition the second alignment sidewall from a ridge of the second alignment sidewall to a surface of a second optic zone of the second optical element; and
cooperatively coupling the alignment sidewall of the first optical element with the alignment sidewall of the second optical element to align an optical axis of the first optical element with an optical axis of the second optical element.

19. The method of claim 18, wherein the first optical element and the second optical element define a cavity disposed between the first optical element and the second optical element when the first alignment sidewall and the second alignment sidewall are cooperatively coupled, the method further comprising providing a liquid crystal into the cavity.

20. The method of claim 18, wherein cooperatively coupling the first alignment sidewall with the second alignment sidewall places a conductive layer being optically transmissive and disposed on the first optic zone and in the pathway defined by the blend zone in conductive communication with a power source.

* * * * *